(12) United States Patent
Liebeskind et al.

(10) Patent No.: US 9,700,881 B2
(45) Date of Patent: Jul. 11, 2017

(54) HETEROCYCLIC COUPLING CATALYSTS AND METHODS RELATED THERETO

(71) Applicant: Emory University, Atlanta, GA (US)

(72) Inventors: Lanny S. Liebeskind, Atlanta, GA (US); Matthew Lindale, Scottdale, GA (US); Pavan Kumar Reddy Gangireddy, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/028,205

(22) PCT Filed: Oct. 8, 2014

(86) PCT No.: PCT/US2014/059606
§ 371 (c)(1),
(2) Date: Apr. 8, 2016

(87) PCT Pub. No.: WO2015/054337
PCT Pub. Date: Apr. 16, 2015

(65) Prior Publication Data
US 2016/0243534 A1    Aug. 25, 2016

Related U.S. Application Data

(60) Provisional application No. 61/945,474, filed on Feb. 27, 2014, provisional application No. 61/893,768, filed on Oct. 21, 2013, provisional application No. 61/888,880, filed on Oct. 9, 2013.

(51) Int. Cl.
| | | |
|---|---|---|
| *B01J 31/02* | (2006.01) | |
| *C07C 269/06* | (2006.01) | |
| *C07C 67/08* | (2006.01) | |
| *C07D 209/20* | (2006.01) | |
| *C07C 231/02* | (2006.01) | |
| *B01J 31/12* | (2006.01) | |
| *B01J 31/16* | (2006.01) | |
| *B01J 31/18* | (2006.01) | |
| *B01J 31/28* | (2006.01) | |
| *C07C 227/04* | (2006.01) | |
| *C07C 49/00* | (2006.01) | |
| *C07D 275/04* | (2006.01) | |
| *C07D 207/404* | (2006.01) | |
| *C07D 513/04* | (2006.01) | |
| *C07C 45/46* | (2006.01) | |

(52) U.S. Cl.
CPC ....... *B01J 31/0271* (2013.01); *B01J 31/0218* (2013.01); *B01J 31/0247* (2013.01); *B01J 31/12* (2013.01); *B01J 31/16* (2013.01); *B01J 31/18* (2013.01); *B01J 31/28* (2013.01); *C07C 45/46* (2013.01); *C07C 49/00* (2013.01); *C07C 67/08* (2013.01); *C07C 227/04* (2013.01); *C07C 231/02* (2013.01); *C07C 269/06* (2013.01); *C07D 207/404* (2013.01); *C07D 209/20* (2013.01); *C07D 275/04* (2013.01); *C07D 513/04* (2013.01)

(58) Field of Classification Search
CPC .. B01J 31/027; B01J 31/0247; B01J 31/0218; C07D 209/20; C07C 231/02; C07C 67/08; C07C 269/06
USPC ........................................................ 548/495
See application file for complete search history.

(56) References Cited

PUBLICATIONS

Rossi et al., Selective Formation of Secondary Amindes via the Copper-Catalyzed Cross-Coupling of Alkylboronic Acids with Primary Amides, 2013, Organic Letters, vol. 15, No. 9, 2314-2317.*
Beletskaya et al. Copper in cross-coupling reactions The post-Ullmann chemistry, Coordination Chemistry Reviews 248 (2004) 2337-2364.
Bhakuni et al. An efficient copper mediated synthetic methodology for benzoldlisothiazol-3(2H)-ones and related sulfur-nitrogen heterocycles, Tetrahedron Letters 53 (2012) 1354-1357.
But et al. The Mitsunobu Reaction: Origin, Mechanism, Improvements, and Applications, Chem. Asian J. 2007, 2, 1340-1355.
Ghosh et al. Copper-Catalyzed Oxidative Amidation of Aldehydes with Amine Salts: Synthesis of Primary, Secondary, and Tertiary Amides J. Org. Chem., 2012, 77, 8007-8015.
Henke et al. Thioimides: New Reagents for Effective Synthesis of Thiolesters from Carboxylic Acids, J. Org. Chem. 2008, 73, 7783-7784.
Jiang et al. Copper-catalyzed C-N bond formation through C-H/N-H activation: a novel approach to the synthesis of multisubstituted ureas, Chem. Commun., 2013, 49, 819.
Liebeskind et al. A Copper-Catalyzed, pH-Neutral Construction of High-Enantiopurity Peptidyl Ketones from Peptidic S-Acylthiosalicylamides in Air at Room Temperature, Angew. Chem. Int. Ed. 2009, 48, 1417-1421.
Mukaiyama, Oxidation-Reduction Condensation, Angew. Chem. Inr. Ed. Engl. vol. 15 (1976) No. 2, 94-103.
Rossi et al. Selective Formation of Secondary Amides via the Copper-Catalyzed Cross-Coupling of Alkylboronic Acids with Primary Amides, Org. Lett., 2013, 15 (9), pp. 2314-2317.
Varela et al. Mechanistic Insights into the Aerobic Cu(I)-Catalyzed Cross-Coupling of S-Acyl Thiosalicylamide Thiol Esters and Boronic Acids, Organometallics. 2012, 31(22): 7958-7968.
Veliz et al. Mitsunobu reactions of nucleoside analogs using triisopropyl phosphite-DIAD, Tetrahedron Letters 47 (2006)3153-3156.
Wang et al. Copper-Catalyzed Intramolecular N-S Bond Formation by Oxidative Dehydrogenative Cyclization, J. Org. Chem. 2013, 78, 7337-7342.

(Continued)

*Primary Examiner* — Kristin Vajda
(74) *Attorney, Agent, or Firm* — Emory Patent Group

(57) ABSTRACT

This disclosure relates to synthetic coupling methods using a catalytic molecule comprising two bonded atoms wherein one atom is an amide nitrogen and the second atom is not nitrogen or carbon, such as sulfur, such as a sufur amide nitrogen bond, typically in a heterocycle, such as substituted benzoisothiazolones and derivatives thereof, as a catalyst in the transformation of hydroxy group containing compounds to amides, esters, ketones, and other carbon to heteroatom or carbon to carbon transformations.

19 Claims, 7 Drawing Sheets

(56) References Cited

PUBLICATIONS

Zhang et al. Mobilizing Cu(I) for Carbon-Carbon Bond Forming Catalysis in the Presence of Thiolate. Chemical Mimicking of Metallothioneins, J Am Chem Soc. 2011, 133(16): 6403-6410.

* cited by examiner

HETEROCYCLIC COUPLING CATALYSTS AND METHODS RELATED THERETO

CROSS-REFERENCE TO RELATED APPLICATIONS

This Application is the National Stage of International Application Number PCT/US2014/059606 filed Oct. 8, 2014, which claims priority to U.S. Provisional Application Numbers 61/945,474 filed Feb. 27, 2014, 61/893,768 filed Oct. 21, 2013, and 61/888,880 filed Oct. 9, 2013. The entirety of each of these applications is hereby incorporated by reference for all purposes.

BACKGROUND

Amide bonds are key component in many biological materials and known drugs. For example, Atorvastatin, which blocks the production of cholesterol, and Valsartan, a blockade of angiotensin-II receptors, both contain amide bonds. Mild, efficient and general methods for the construction of amide and peptide linkages are desired for the production of therapeutics and biological tools that are based upon peptide, protein, and glycopeptides motifs.

Amide bonds are typically synthesized from the union of carboxylic acids and amines; however, the reaction between these two functional groups is not spontaneous at ambient temperature, with the elimination of water only taking place at extremely high temperatures (>200° C.), conditions which are typically detrimental to the integrity of the reacting compounds themselves.

Some coupling methods used to generate amide bonds from carboxylic acids and amines utilize special activating protocols or the construction of special functionalities such as azides and ketoacids or hydroxylamines. There are a number of 'coupling reagents' which convert the hydroxy (—OH) of the carboxylic acid to a good leaving group prior to the treatment with the amine. Classical reagents include carbodiimides, phosphonium salts, uronium salts and reagents generating acid halides.

Generating amine reactive acid halides, using reagents such as thionyl chloride and phosphorus pentachloride, is not compatible with many synthetic strategies, due to the formation of hydrochloric acid. Newer reagents used to generate acid halides such as Deoxo-Fluor and DAST are expensive, hazardous, and require purification by chromatography after the reaction.

Carbodiimides such as dicyclohexylcarbodiimide (DCC) are commonly used as coupling reagents; however, these reagents need to be used in conjunction with additives such as 1-hydroxy-1H-benzotriazole (HOBt) or 1-hydroxy-7-azabenzotriazole (HOAt) in order to decrease undesired epimerization that can occur when using chiral amino acids. These additives yield by-products that catalyze the 'dimerization' of DCC. In addition to this, safety considerations have to be carefully considered when using benzotriazoles (or variants thereof) because of their explosive properties.

The coupling reagents based on the HOBt/HOAt system, such as uronium/aminium salts like HATU react with the carboxylic acids to form active esters; however, side reactions of the coupling reagents with the amines lead to the formation of guanidinium side products. The phosphonium salts, which are also based on HOBt/HOAt, such as BOP are undesirable due to the carcinogenic and respiratory toxicity associated with HMPA generated in the reaction.

More recent approaches to amide bond formation include Staudinger ligation, a modification of the Staudinger reaction which produces an amide linked product from the reaction of a modified triarylphosphine and azides, as well as the further modified version which involves the reaction of thioacids with azides.

Another method is the 'native chemical ligation' method which is used for the preparation of proteins. It involves the reaction between a peptide alpha-thioester and a cysteine-peptide, to yield a product with a native amide bond at the ligation site. However, the thioalkyl esters are rather unreactive and despite the use of a catalyst the reaction typically takes 24-28 hours.

Although the above methodologies have been applied to the synthesis of proteins and protein analogues, there is a continued interest in the wider application of the tools of organic chemistry to the study of proteins. Despite the number of coupling reagents that have been reported, most reagents are simply not efficient for a broad range of amide bond forming reactions. Thus, there remains a need for simple, effective reagents with high conversions and low levels of epimerization of chiral compounds that produces limited by-products.

Certain catalytic dehydrative condensation reactions are reported by the reaction of carboxylic acids with alcohols and amines to give esters and amides. See Funatomi et al., Green Chem, 2006, 8, 1022; Ishihara, Tetrahedron, 2009, 65, 1085; and Sakakura et al., JACS, 2007, 129, 14775. See also Mukaiyama et al. ACIE, 1976, 15(2), 94; But et al. Chem. Asian J. 2007, 2, 1340; and Véliz & Beal, Tet Lett, 2006, 47, 3153.

Henke & Srogl report thioimides in relation to the synthesis of thiolesters from carboxylic acids J. Org. Chem. 2008, 73, 7783-7784.

Liebeskind et al., report copper-catalyzed construction of peptidyl ketones from peptidic S-acylthiosalicylamides. ACIE, 2009, 48, 1417-1421. See also Varela-Álvarez, Organometallics, 2012, 31, 7958; Liebeskind, J. Am. Chem. Soc., 2000, 122, 11260-11261; and Wittenberg et al. Org. Lett. 2003, 5, 3033-3035, Zhang et al. report mobilizing Cu(I) for carbon-carbon bond forming catalysis in the presence of thiolate. J Am Chem Soc., 2011, 133(16): 6403-6410.

Wang et al. report copper-catalyzed intramolecular N—S bond formation by oxidative dehydrogenative cyclization. J. Org. Chem., 2013, 78, 7337-7342.

References cited herein are not an admission of prior art.

SUMMARY

This disclosure relates to synthetic coupling methods using a catalytic molecule comprising two bonded atoms wherein one atom is nitrogen or an amide nitrogen and the second atom is not nitrogen or carbon, such as sulfur, such as a sufur amide nitrogen bond, typically in a heterocycle, such as substituted benzoisothiazolones and derivatives thereof, as a catalyst in the transformation of hydroxy group containing compounds to amides, esters, ketones, and other carbon to heteroatom or carbon to carbon transformations.

In certain embodiments, the disclosure relates to methods of catalyzing a coupling reaction comprising mixing a) a compound comprising a hydroxy group, b) a trisubstituted phosphite, c) a nucleophile, and d) a catalytic heterocycle comprising two bonded heteroatoms wherein one heteroatom is a nitrogen eor an amide nitrogen and the second heteroatom is not nitrogen, such as a sulfur, amide heterocycle, under conditions such that a compound is formed comprising the nucleophile in place of the hydroxy group. In certain embodiments the reaction is catalyzed in aerobic conditions.

In certain embodiments, the compound comprising a hydroxy group is the hydroxy group of a carboxylic acid. In certain embodiments, the carboxylic acid compound is an amino acid, protected amino acid, nucleotide, polynucleotide, polypeptide, or polypeptide. In certain embodiments, carboxylic acid compound is linked to a solid support.

In certain embodiments, mixing includes the addition of copper. In certain embodiments, mixing includes the addition of a nitrogen containing copper ligand selected from N-methylimidazole, N-methylmorpholine, N,N'-dimethylaminopyridine, 1,4-diazabicyclo[2.2.2]octane, and methylpyridine.

In certain embodiments, the trisubstituted phosphite is trialkylphosphite selected from trimethylphosphite, triethylphosphite, tripropylphosphite, triisopropylphosphite, tributyl phosphite, and tert-butylphoshpite.

In certain embodiments, mixing is done under conditions such that an amide, an amine, an ester, an ether, a ketone, or other carbon to carbon bond is formed.

In certain embodiments, the compound comprising a hydroxy group is primary or secondary alcohol or a carboxylic acid.

In certain embodiments, the nucleophile comprising a hydrogen group is a primary or secondary amine, or primary or secondary alcohol, or boronic acid.

In certain embodiments, the catalyst comprising a sulfur nitrogen heterocycle is benzoisothiazolone or derivative thereof.

In certain embodiments, the catalytic heterocycle is linked through a linking group to a silicate, glass, polymer, metal, particle, nanoparticle, magnetic bead, nanostructure, or other solid support.

DETAILED DISCUSSION

Figure 1:
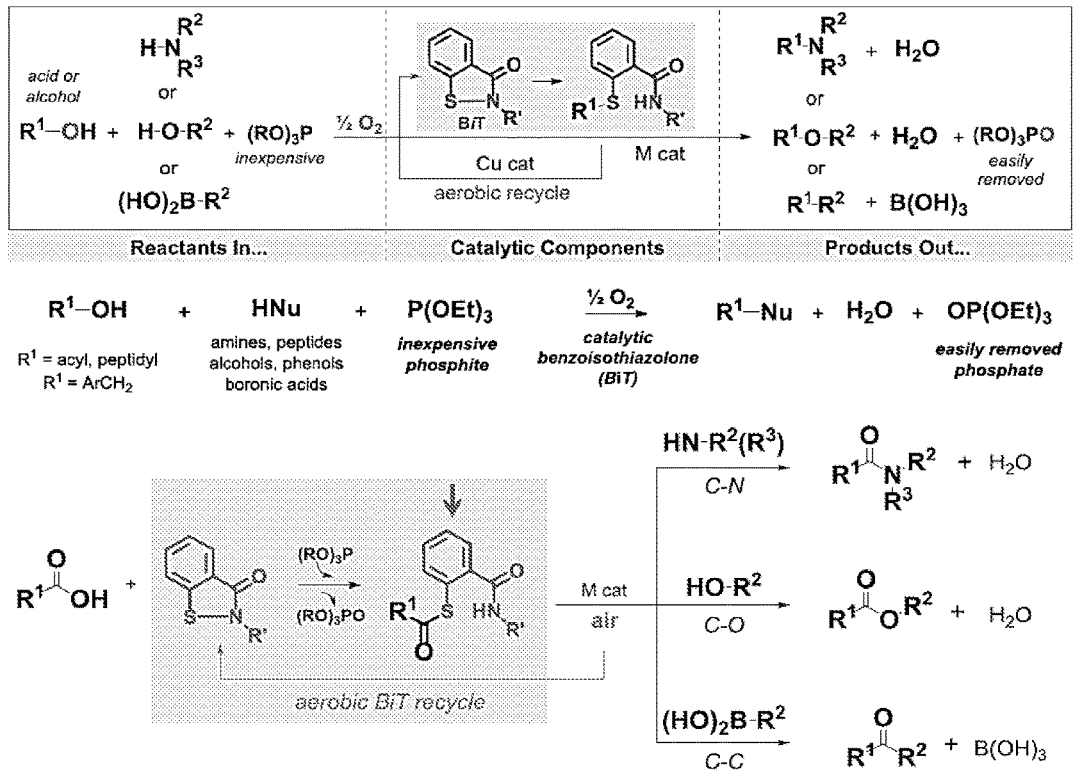
FIG. 1 illustrates certain embodiments disclosed herein for benzoisothiazolone (BiT)-catalyzed, redox-coupled dehydrative bond formation. Three steps include redox dehydration of $R^1$—OH to a thioorganic intermediate, aerobic condition desulfitative coupling to create the C—N, C—O, or C—C product, and aerobic regeneration of the BiT catalyst 1. Typical reaction conditions include mixing in solvent under $N_2$ or Ar, adding 4 Å mol sieves, stirring between room temp and 50° C., evaporating and triturating or partitioning between $H_2O$/EtOAc. Typical reaction solvents include THF, DMF, toluene, EtOAc, $CH_3CN$.
Figure 2:
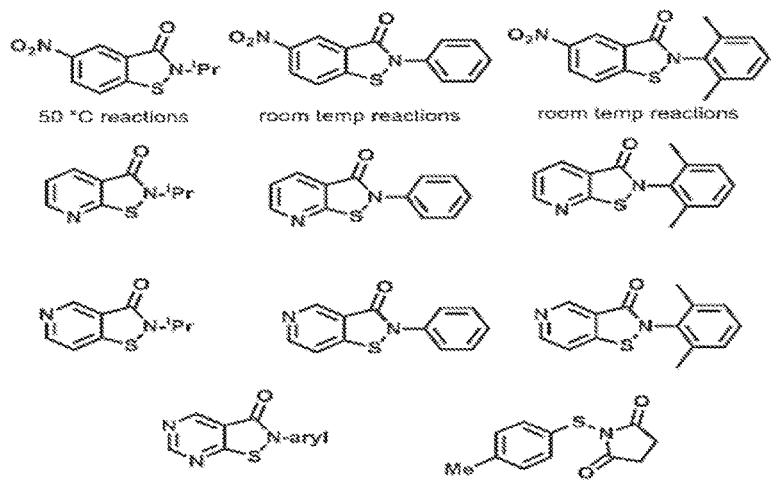
FIG. 2 illustrates embodiments of catalyst comprising a sulfur nitrogen heterocycle such as benzoisothiazolone and derivatives thereof.
Figure 3:
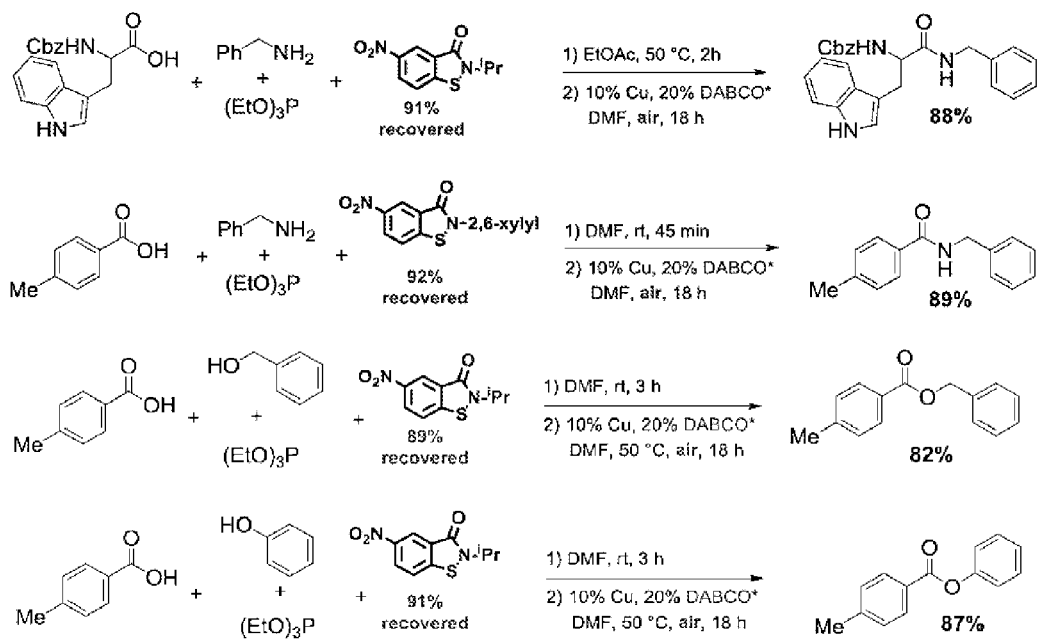
FIG. 3 illustrates conditions for BiT-catalyzed aerobic amidations.
Figure 4:
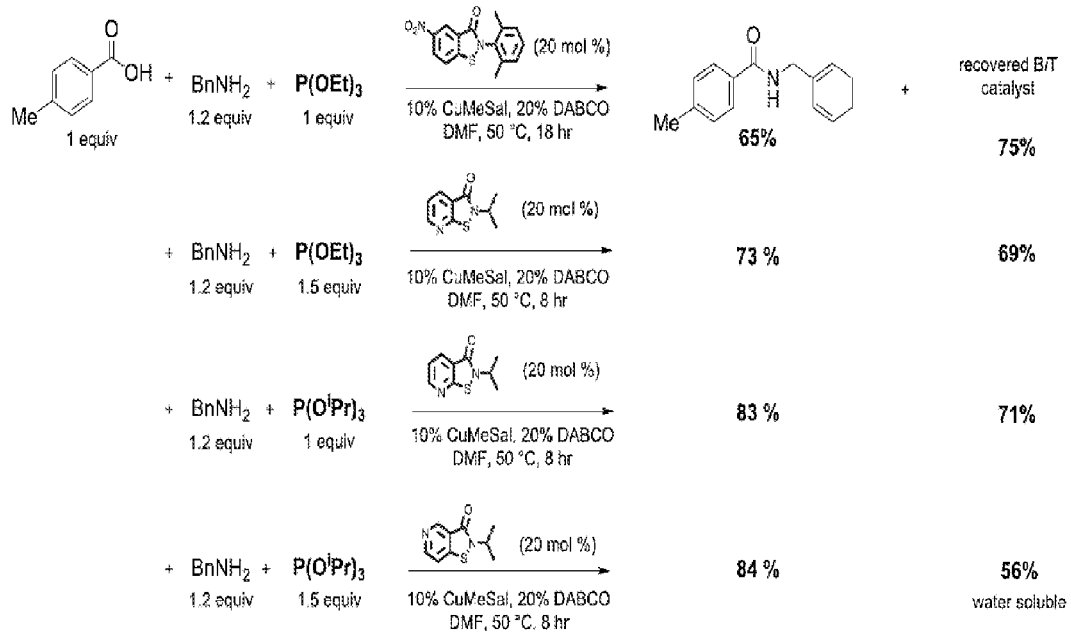
FIG. 4 illustrates conditions for BiT-catalyzed aerobic amidations. The observed reaction rate varies with the nature of the BiT: 2- and 4-pyridyl BiT's are fastest. Lower Cu-DABCO loadings are contemplated. Background oxidation of phosphite is slow; thus, it is not problematic for the faster reactions.
Figure 5:
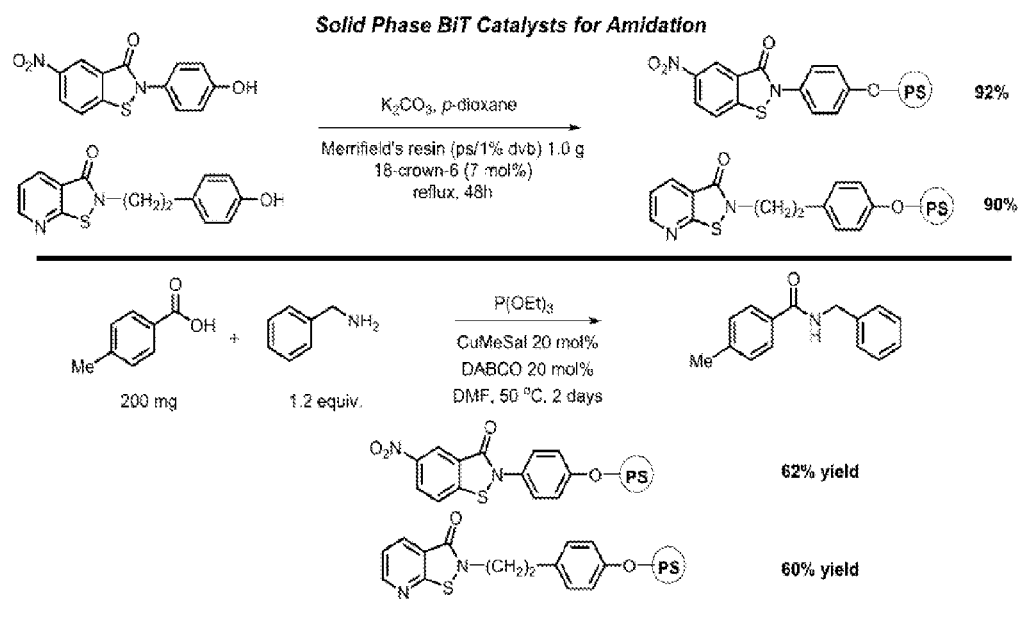
FIG. 5 illustrates solid phase BiT catalysts.
Figure 5:
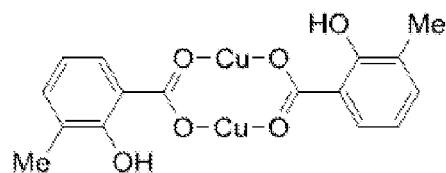
Figure 6:
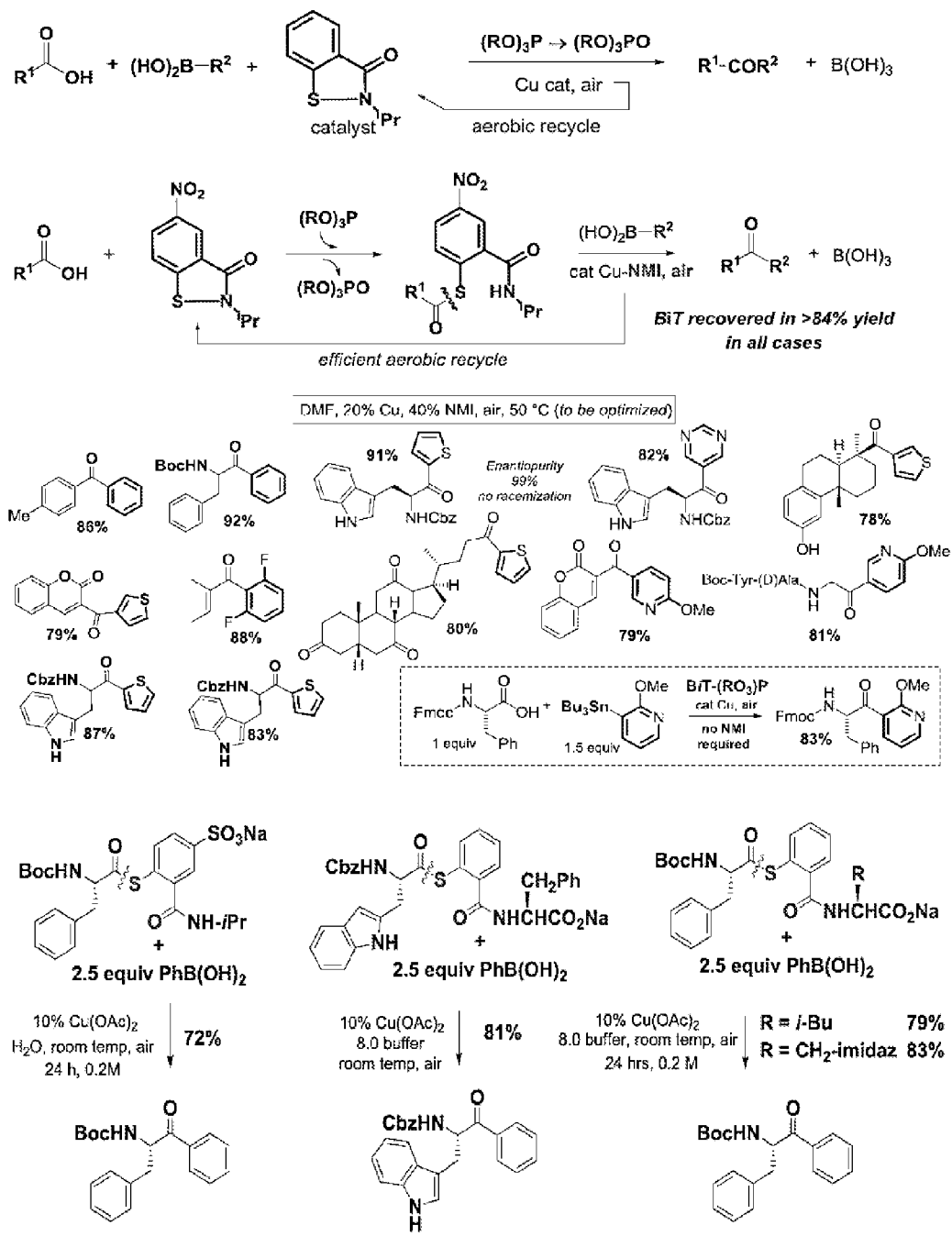
FIG. 6 illustrates conditions for esterification and ketonization.
Figure 7:
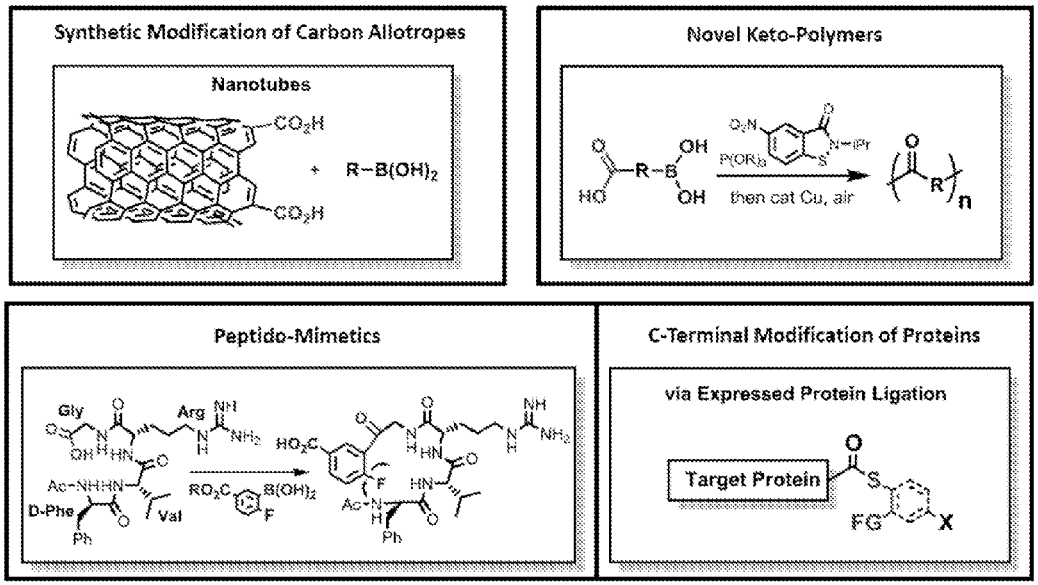
FIG. 7 illustrates additional embodiments of the disclosure.
Figure 8:
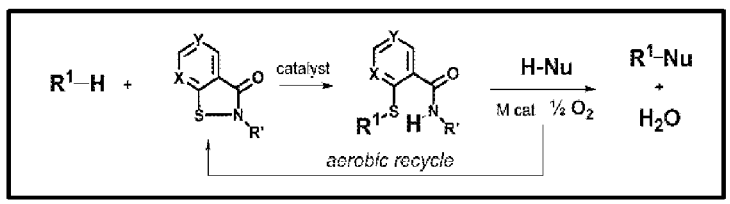
FIG. 8 illustrates methods of alkylative dehydration.
Figure 8:
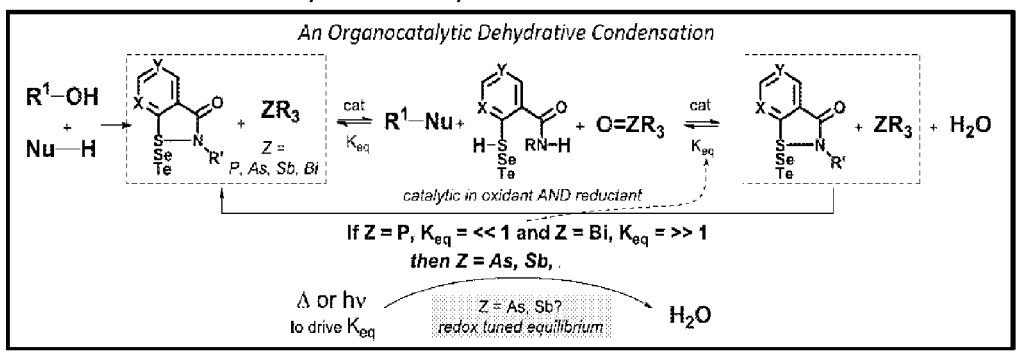
Figure 8:
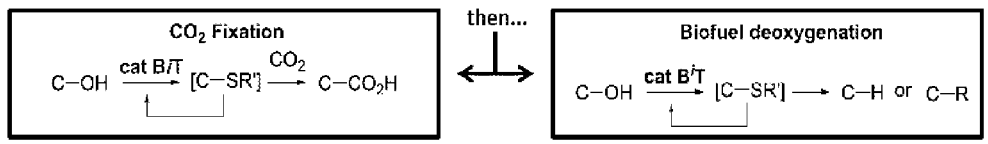
Figure 9:
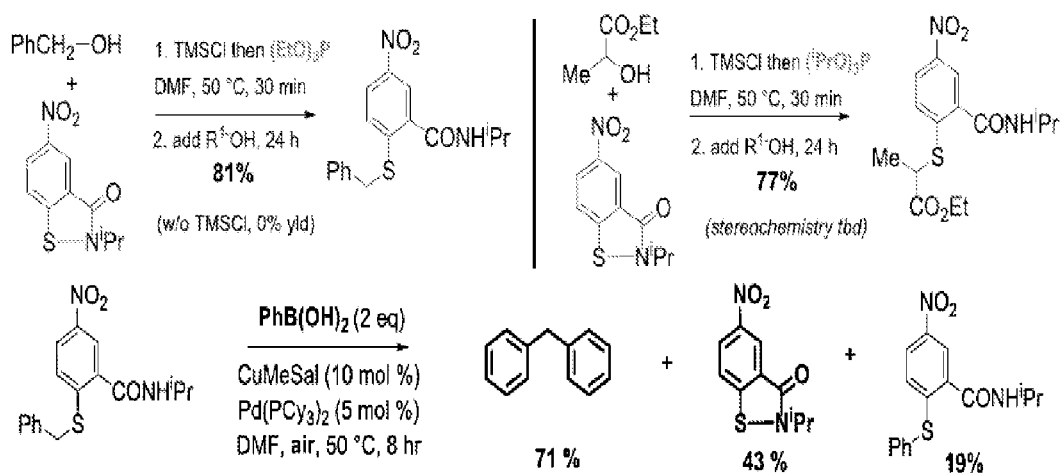
FIG. 9 illustrates conditions for alkylative dehydration.
Figure 9:
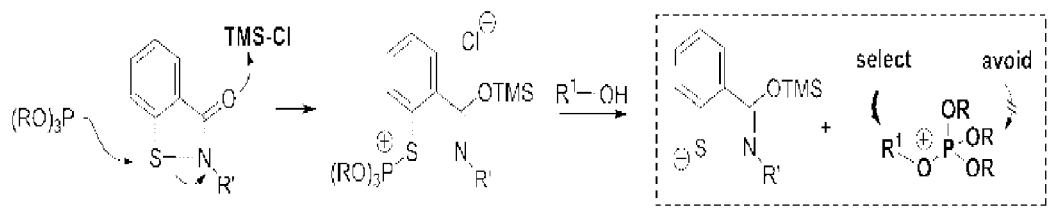

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Terms

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, the term "amino acid" refers to both naturally-occurring and synthetically modified (D-, L-, achiral or racemic) amino acids and derivatives. In some embodiments, the amino acid may be selected from the group consisting of any one or more of (D-, L-, achiral or racemic) glycine, alanine, valine, leucine, isoleucine, phenylalanine, serine, methionine, proline, tyrosine, tryptophan, lysine, arginine, histidine, aspartate, glutamate, asparagine, glutamine, cysteine, methionine, hydroxyproline, gama-carboxyglutamate, O-phosphoserine, ornithine, homoarginine and various protected derivatives thereof.

A "protecting group" refers to those moieties that are introduced into a molecule by chemical modification of a functional group in order to obtain chemoselectivity in a subsequent chemical reaction. Examples include, but are not limited to, 4-methoxy-2,3,6-trimethylphenyl)sulfonyl (Mtr), 2,2,5,7,8-pentamethyl-chroman-6-sulphonyl (Pmc), tosyl (Tos), mesitylenesulfonyl (Mts), 4,4'-dimethoxybenzhydryl (Mbh), 2,4,6-trimethoxybenzyl (Tmob), tripheylmethyl (Trt), 9-fluorenylmethyloxycarbonyl (fmoc), tert-buty (tBu), benzyl (Bzl), t-Butoxymethyl ether (Bum), (2,4-dinitrophenol) Dnp, benzyloxymethyl (Bom), benzyloxycarbonyl (Z), 2-chloro-benzyloxycarbonyl (CIZ), t-butyloxycarbonyl (Boc), formyl (CHO) or 2-bromobenzyloxycarbonyl (BrZ) and heterocycles such as succinimide, maleimide, and phathalimide.

As used herein, a "linker" refers to any molecular configuration that joins molecular moieties. It includes molecules with covalent and non-covalent interactions. A prefer linker is a polymer, i.e., molecule with repeated linking moieties. The linked moieties may be identical in structure or vary, e.g., copolymers. Linking polymers include, but are not limited to, biological polymers, polyethylene glycols, alkylacrylates, alkylacrylamides, and substituted variants.

"Saccharide" refers a sugar(s) or substituted sugar(s) exemplified by, but not limited to, ribose, riboside, glucose, glucoside, mannose, mannoside, mannoside, galactose, galactoside, talitol, taloside, rhamnitol, rhamnoside, maltose, maltoside, 2,3-dideoxyhex-2-enopyranoside, 2,3-desoxy-2,3-dehydroglucose, 2,3-desoxy-2,3-dehydroglucose diacetate, 2,3-desoxy-2,3-dehydromaltoside, 2,3-desoxy-2,3-dehydromaltoside pentaacetate, 2,3-desoxymaltoside, lactoside, lactoside tetraacetate, 2,3-desoxy-2,3-dehydrolactoside, 2,3-desoxy-2,3-dehydrolactoside pentaacetate, 2,3-desoxylactoside, glucouronate, N-acetylglucosamine, fructose, sorbose, 2-deoxygalactose, 2-deoxyglucose, maltulose, lactulose, palatinose, leucrose, turanose, lactose, mannitol, sorbitol, dulcitol, xylitol, erythitol, threitol, adonitol, arabitol, 1-aminodulcitol, 1-aminosorbitol, isomaltitol, cellobiitol, lactitol, maltitol, volemitol perseitol, glucoheptitiol, alpha,alpha-glucooctitiol or combinations thereof, i.e., disaccharides, polysaccharides, and carbohydrates. Saccharides can be derivatized with molecular arrangements that facilitate synthesis (i.e., contain a protecting group, e.g., acetyl group).

The term "substrate" refers to any variety of solid surfaces. The solid surfaces may be provided in a variety of formats. For examples, the substrates may be planar or curved surfaces or be beads. In some preferred embodiments, the beads are commercially available beads such as glass beads, agarose beads, acrylic beads, plastic, or latex beads. In some embodiments, the beads are magnetic. In still other embodiments, the beads are coated with organic film(s) or metal(s) such as silver or gold. A wide variety of reaction types are available for the functionalization of solid surfaces. For example, solid surfaces constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized solid surfaces can be made from etched, reduced polytetrafluoroethylene.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. Contemplated derivative include switching carbocyclic, aromatic or phenyl rings with heterocyclic rings or switching heterocyclic rings with carbocyclic, aromatic or phenyl rings, typically of the same ring size. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, all hereby incorporated by reference.

A "silylating agent" refers to an variety of silicon based reagents typically used to form a silicon bond with atoms such as oxygen, nitrogen, and sulfur, including, but not limited to, N-methyl-N-(trimethylsilyl)trifluoroacetamide, N-tert-butyldimethylsilyl-N-methyltrifluoroacetamide, 1,3-bis(chloromethyl)-1,1,3,3-tetramethyldisilazane, 1-(trimethylsilyl)imidazole, 3-trimethylsilyl-2-oxazolidinone, allyl (chloro)dimethylsilane, bromotrimethylsilane, chlorotriethylsilane, chlorotriisopropylsilane, chlorotrimethylsilane, hexaethyldisiloxane, hexamethyldisilazane, N,N'-bis(trimethylsilyl)urea, N,N-dimethyltrimethylsilylamine, N,O-bis(trimethylsilyl)acetamide, N-methyl-N-trimethylsilylacetamide, N-methyl-N-trimethylsilylheptafluorobutyramide, trimethylsilyl methanesulfonate, trimethylsilyl N,N-dimethylcarbamate, trimethylsilyl trifluoromethanesulfonate, triphenylsilane, methyl 3-trimethylsiloxy-2-butenoate, phenylchlorosilane, or triethylsilane or mixtures thereof. In certain embodiments, the silylating agent is intended to include molecules comprising of Si—S units such as silylthiols and silathianes, e.g., hexamethyldisilathiane (HMDST).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced.

Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

When used in reference to compound(s) disclosed herein, "salts" refer to derivatives of the disclosed compound(s) where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfamoyl" refers to an alkyl as defined above attached through a sulfamoyl bridge (i.e., —S(=O)$_2$NHalkyl), and an "Arylsulfamoyl" refers to an alkyl attached through a sulfamoyl bridge (i.e., —S(=O)$_2$NHaryl).

"Alkylsulfinyl" refers to an alkyl as defined above with the indicated number of carbon atoms attached through a sulfinyl bridge (i.e. —S(=O)alkyl).

The terms "halogen" and "halo" refer to fluorine, chlorine, bromine, and iodine.

The term "aroyl" refers to an aryl group (which may be optionally substituted as described above) linked to a carbonyl group (e.g., —C(O)-aryl).

"Sulfoxy" referes to sulphonic acid attached through an oxygen bridge (i.e., —O—S(=O)$_2$O).

The term "sulfonate" refers to salt of sulfonic acid or ester theref. (i.e., —S(=O)$_2$O$^-$ cation$^+$-S(=O)$_2$OR).

"Ester" refers to as the oxygen bridge between two carbon atoms, wherein neither of the bridged carbon atom are a carbonyl (i.e., oxo substituted).

An unspecified "R" group is a lower alkyl, aryl, or heteroaryl, which may be optionally substituted with one or more, the same or different, substituents.

Throughout the specification, groups and substituents thereof may be chosen to provide stable moieties and compounds.

Catalytic Molecules

This disclosure relates to synthetic coupling methods using catalytic molecules containing a sulfur nitrogen bond, such as a sufur amide nitrogen bond, typically in a heterocycle, such as substituted benzoisothiazolones and derivatives thereof, as catalysts in the transformation of hydroxy group containing compounds to amides, esters, ketones, and other carbon to heteroatom or carbon to carbon transformations.

In certain embodiments, the disclosure relates to methods and compositions comprising the catalytic heterocycle.

In certain embodiments, the catalytic heterocycle has the following formula:

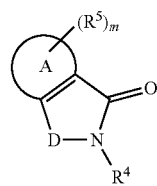

or salts thereof wherein,
A is an aryl or heteroaryl ring;
D is sulfur, selenium, or tellurium;
m is 0, 1, 2, 3, or 4;

R⁴ is selected from alkyl, alkenyl, alkanoyl, cyano, dialkylamino, carbocyclyl, aryl, and heterocyclyl wherein R⁴ is optionally substituted with one or more, the same or different, $R^{40}$ or $R^{41}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is at each occurrence individually selected from alkyl, alkenyl, alkanoyl, halogen, nitro, suflonate, cyano, hydroxy, amino, mercapto, formyl, carboxy, sulfoxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, D is sulfur.

In certain embodiments, the catalytic hetercycle has the following formula:

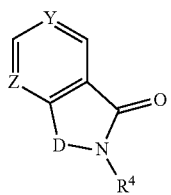

wherein,
D is sulfur, selenium, or tellurium;
Y is N, CH, or C—$R^5$;
Z is N or CH
R⁴ is selected from alkyl, alkenyl, alkanoyl, cyano, dialkylamino, carbocyclyl, aryl, and heterocyclyl wherein R⁴ is optionally substituted with one or more, the same or different, $R^{40}$ or $R^{41}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^5$ is an electron with drawing group selected from nitro, sulfonate, quaternary amine, trihalo alkyl, trifluoromethyl, cyano, alkanoyl, formyl, carboxy, carbamoyl, alkylsulfinyl, alkylsulfonyl, and arylsulfonyl wherein $R^5$ is optionally substituted with one or more, the same or different, $R^{50}$.

In certain embodiments, the catalytic hetercycle has the following formula:

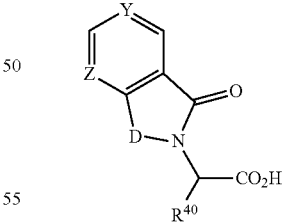

wherein,
D is sulfur, selenium, or tellurium;
Y is N, CH, or C—$R^5$;
Z is N or CH;
$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^5$ is an electron with drawing group selected from nitro, sulfonate, quaternary amine, trihalo alkyl, trifluoromethyl, cyano, alkanoyl, formyl, carboxy, carbamoyl, alkylsulfinyl, alkylsulfonyl, and arylsulfonyl wherein $R^5$ is optionally substituted with one or more, the same or different, $R^{50}$.

Methods of Use

In certain embodiments, the disclosure relates to methods of catalyzing a coupling reaction comprising mixing a) a compound comprising a hydroxy group, b) a trisubstituted phosphite, c) a nucleophile, and d) a catalytic molecule comprising two bonded atoms wherein one atom is an amide nitrogen and the second atom is not nitrogen, such as a sulfur, under conditions such that a compound is formed comprising the nucleophile in place of the hydroxy group.

In certain embodiments, the catalytic molecule comprising two bonded atoms wherein one atom is an amide nitrogen and the second atom is not nitrogen is a catalytic heterocycle comprising two bonded heteroatoms wherein one heteroatom is an amide nitrogen and the second heteroatom is not nitrogen, such as a sulfur, amide heterocycle, In certain embodiments, the disclosure relates to methods of forming an amide or ester comprising mixing
 a) a compound comprising a carboxylic acid,
 b) a trialkylphosphite,
 c) an amine or an alcohol,
 d) a sulfur, amide heterocycle, and
 e) copper,
 under conditions such that an amide or an ester is formed.

Further embodiments include the synthesis of simple as well as complex cyclic and acyclic peptides, the construction of glycopeptides, for peptide ligation.

The reagents disclosed herein may also be employed to ligate an amino acid, peptide or protein group to a carbohydrate group, which may be a mono-, di-, tri- or polysaccharide, or to a nucleoside. The reagents of this disclosure may also be employed to ligate an amino acid, a peptide or protein group to a reporter group, tag or label (e.g., a group whose presence can be detected by optical or mass spectrometry or other instrumental method), including a fluorescent or phosphorescent group, an isotopic label or a radiolabel.

The chemistry of the present disclosure may be suitably employed for the formation of cyclic peptides as well for macrolactamization reactions.

In certain embodiments, the compound comprising a carboxylic acid, has the following formula:

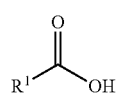

wherein, $R^1$ is selected from alkyl, alkenyl, alkanoyl, cyano, carboxy, alkylamino, dialkylamino, carbocyclyl, aryl, heterocyclyl, amino acid, polypeptide and wherein $R^1$ is optionally substituted with one or more, the same or different, $R^{10}$ or $R^{15}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$ or $R^{15}$;

$R^{11}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with one or more, the same or different, $R^{12}$ or $R^{15}$;

$R^{12}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{12}$ is optionally substituted with one or more, the same or different, $R^{13}$ or $R^{15}$;

$R^{13}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{13}$ is optionally substituted with one or more, the same or different, $R^{14}$ or $R^{15}$;

$R^{14}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with one or more, the same or different, $R^{15}$; and $R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In some embodiments, a compound comprising a hydroxy group is a compound comprising the following formula:

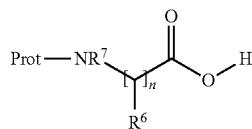

or salts thereof wherein,

Prot is a protecting group, peptide, or linker to a substrate or biological material, or $R^8$;

n is 1, 2, 3, 4, 5, or 6;

each $R^6$ is independently selected from hydrogen, alkyl, hydroxyalkyl, thiolalkyl, aminoalkyl, selenoalkyl, carboxylalkyl, aryl, or heterocyclyl, and wherein $R^6$ is optionally substituted by one or more, the same or different, $R^{60}$;

$R^7$ is hydrogen, alkyl, acyl, or $R^7$ and Prot and the attached atoms form a protecting group comprising a 4 to 7 member heterocyclic ring such as a succinimide, maleimide, or phthalimide which may be substituted with one or more, the same or different, substituents, such as one or more, the same or different, $R^{60}$ or or $R^6$ and $R^7$ and the atoms to which they are attached to form a 4-7 membered heterocyclic ring optionally substituted with one or more, the same or different, $R^{60}$;

$R^{60}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{60}$ is optionally substituted with $R^{61}$;

$R^{61}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl; and $R^8$ is alkyl, alkanoyl, formyl, alkylcarboxy, alkylcarbamoyl wherein $R^8$ is optionally substituted with one or more, the same or different, $R^{80}$;

$R^{80}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{80}$ is optionally substituted with one or more, the same or different, $R^{81}$; and $R^{81}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^6$ and $R^7$ or $R^7$ and Prot form a 5 or 6 membered ring.

In certain embodiments, Prot is tert-butoxycarbonyl (Boc) or fluorenylmethyloxycarbonyl (Fmoc).

In certain embodiments, n is 1 or 2.

In certain embodiments, the biological material is a peptide, enzyme, receptor, nucleic acid, cell, antibody, saccharide, polysaccharide, or glycopeptide.

In certain embodiments, the linker is a peptide, a nucleic acid, hydrocarbon, polyethylene glycol, polysaccharide, acrylate polymer, or other polymer.

In some embodiments, a compound comprising a hydroxy group selected from N-alpha-Boc-alanine, N-beta-Boc-beta-alanine, N-alpha-Boc-N-alpha-methyl-alanine, N-alpha-Boc-alpha-aminobutyric acid, N-Boc-4-aminobutanoic acid, N-alpha-Boc-alpha-aminoisobutyric acid, N-alpha-Boc-$N^G$-(4-Methoxy-2,3,6 trimethylbenzenesulfonyl)-arginine, N-alpha-Boc-$N^G$-nitro-arginine, N-alpha-Boc-$N^G$-tosyl-arginine, N-alpha-Boc-$N^G$,$N^G$-bis-CBZ-arginine, N-alpha-Boc-asparagine, N-alpha-Boc-asparagine, N-alpha-Boc-beta-trityl-asparagine, N-alpha-Boc-N-beta-xanthyl-asparagine, N-alpha-Boc-isoasparagine-, N-alpha-Boc-aspartic acid beta-1-adamantyl ester, N-alpha-Boc-aspartic acid beta-2-adamantyl ester, N-alpha-Boc-aspartic acid alpha-benzyl ester, N-alpha-Boc-N-alpha-methyl-valine, N-alpha-Boc-valine, N-Boc-6-aminohexanoic acid, N-alpha-Boc-tert-leucine, N-alpha-Boc-S-acetamidomethyl-cysteine, N-alpha-Boc-S-benzyl-cysteine, N-alpha-Boc-S-p-methylbenzyl-cysteine, N-alpha-Boc-S-p-methoxybenzyl-cysteine, N-alpha-Boc-S-trityl-cysteine, N-alpha-Boc-beta-cyclohexyl-alanine, N-alpha-Boc-glutamic acid alpha-benzyl ester, N-alpha-Boc-glutamic acid gama-benzyl ester, N-alpha-Boc-glutamic acid gama-cyclohexyl ester, N-alpha-Boc-glutamic acid gama-tert-butyl ester, N-alpha-Boc-gama-trityl-glutamine, N-alpha-Boc-gama-xanthyl-glutamine, N-alpha-N-im-di-Boc-histidine, N-alpha-Boc-N-im-tosyl-histidine, N-alpha-Boc-N-im-dinitrophenyl-histidine, N-alpha-Boc-N-im-trityl-histidine, N-alpha-Boc-trans-4-hydroxyproline, N-alpha-Boc-glycine, N-alpha-Boc-isoleucine, N-alpha-Boc-N-epsilon-acetyl-lysine, N-alpha,epsilon-di-Boc-lysine, N-alpha-Boc-N-epsilon-2-chloro-CBZ-lysine, N-alpha-Boc-N-epsilon-trifluoroacetyl-lysine, N-alpha-Boc-leucine, N-alpha-Boc-methionine-sulfone, N-alpha-Boc-methionine, N-alpha-Boc-methionine-sulfoxide, N-alpha-Boc-N-alpha-methyl-norleucine, N-alpha-Boc-norleucine, N-alpha-Boc-norvaline, N-alpha-Boc-3,4-dehydro-proline, N-alpha-Boc-proline, N-alpha-Boc-N-alpha-methyl-phenylalanine, N-alpha-Boc-4-chloro-phenylalanine, N-alpha-Boc-phenylalanine, N-alpha-Boc-phenylglycine, N-alpha-Boc-N-δ-benzyloxycarbonyl-ornithine, N-alpha-Boc-sarcosine, N-alpha-Boc-O-benzyl-serine, N-alpha-Boc-O-methyl-serine, N-alpha-Boc-O-tert-butyl-serine, N-1-Boc-1,2,3,4,-tetrahydro-isoquinoline-3-carboxylic acid alpha, N-alpha-Boc-N-in-Boc-trypophan, N-alpha-Boc-N-in-formyl-tryptophan, N-alpha-Boc-N-in-mesitylene-2-sulfonyl-tryptophan, N-alpha-Boc-tyrosine, N-alpha-Boc-N-alpha-methyl-O-benzyl-tyrosine, N-alpha-Boc-O-2-bromobenzyloxycarbonyl-tyrosine, N-alpha-Boc-O-benzyl-tyrosine, N-alpha-Boc-O-2,6-dichlorobenzyl-tyrosine, N-alpha-Boc-O-ethyl-tyrosine, N-alpha-Boc-O-methyl-tyrosine, N-alpha-Boc-O-tert-butyl-tyrosine, N-alpha-Boc-O-benzyl-threonine, and N-alpha-Boc-threonine, N-alpha-Fmoc-alanine, N-beta-Fmoc-beta-alanine, N-alpha-Fmoc-N-alpha-methyl-alanine, N-alpha-Fmoc-alpha-aminobutyric acid, N-Fmoc-4-aminobutanoic acid, N-alpha-Fmoc-alpha-aminoisobutyric acid, N-alpha-Fmoc-$N^G$-(4-Methoxy-2,3,6 trimethylbenzenesulfonyl)-arginine, N-alpha-Fmoc-$N^G$-nitro-arginine, N-alpha-Fmoc-$N^G$-tosyl-arginine, N-alpha-Fmoc-$N^G,N^G$-bis-CBZ-arginine, N-alpha-Fmoc-asparagine, N-alpha-Fmoc-asparagine, N-alpha-Fmoc-beta-trityl-asparagine, N-alpha-Fmoc-N-beta-xanthyl-asparagine, N-alpha-Fmoc-isoasparagine, N-alpha-Fmoc-aspartic acid beta-1-adamantyl ester, N-alpha-Fmoc-aspartic acid beta-2-adamantyl ester, N-alpha-Fmoc-aspartic acid alpha-benzyl ester, N-alpha-Fmoc-N-alpha-methyl-valine, N-alpha-Fmoc-valine, Fmoc-6-aminohexanoic acid, N-alpha-Fmoc-tert-leucine, N-alpha-Fmoc-S-acetamidomethyl-cysteine, N-alpha-Fmoc-S-benzyl-cysteine, N-alpha-Fmoc-S-p-methylbenzyl-cysteine, N-alpha-Fmoc-S-p-methoxybenzyl-cysteine, N-alpha-Fmoc-S-trityl-cysteine, N-alpha-Fmoc-beta-cyclohexyl-alanine, N-alpha-Fmoc-glutamic acid alpha-benzyl ester, N-alpha-Fmoc-glutamic acid gama-benzyl ester, N-alpha-Fmoc-glutamic acid gama-cyclohexyl ester, N-alpha-Fmoc-glutamic acid gama-tert-butyl ester, N-alpha-Fmoc-gama-trityl-glutamine, N-alpha-Fmoc-gama-xanthyl-glutamine, N-alpha-N-im-di-Fmoc-histidine, N-alpha-Fmoc-N-im-tosyl-histidine, N-alpha-Fmoc-N-im-dinitrophenyl-histidine, N-alpha-Fmoc-N-im-trityl-histidine, N-alpha-Fmoc-trans-4-hydroxyproline, N-alpha-Fmoc-glycine, N-alpha-Fmoc-isoleucine, N-alpha-Fmoc-N-epsilon-acetyl-lysine, N-alpha,epsilon-di-Fmoc-lysine, N-alpha-Fmoc-N-epsilon-2-chloro-CBZ-lysine, N-alpha-Fmoc-N-epsilon-trifluoroacetyl-lysine, N-alpha-Fmoc-leucine, N-alpha-Fmoc-methionine-sulfone, N-alpha-Fmoc-methionine, N-alpha-Fmoc-methionine-sulfoxide, N-alpha-Fmoc-N-alpha-methyl-norleucine, N-alpha-Fmoc-norleucine, N-alpha-Fmoc-norvaline, N-alpha-Fmoc-3,4-dehydro-proline, N-alpha-Fmoc-proline, N-alpha-Fmoc-N-alpha-methyl-phenylalanine, N-alpha-Fmoc-4-chlorophenylalanine, N-alpha-Fmoc-phenylalanine, N-alpha-Fmoc-phenylglycine, N-alpha-Fmoc-N-δ-benzyloxycarbonyl-ornithine, N-alpha-Fmoc-sarcosine, N-alpha-Fmoc-O-benzyl-serine, N-alpha-Fmoc-O-methyl-serine, N-alpha-Fmoc-O-tert-butyl-serine, N-1-Fmoc-1,2,3,4,-tetrahydro-isoquinoline-3-carboxylic acid, N-alpha-Fmoc-N-in-Fmoc-trypophan, N-alpha-Fmoc-N-in-formyl-tryptophan, N-alpha-Fmoc-N-in-mesitylene-2-sulfonyl-tryptophan, N-alpha-Fmoc-tyrosine, N-alpha-Fmoc-N-alpha-methyl-O-benzyl-tyrosine, N-alpha-Fmoc-O-2-bromobenzyloxycarbonyl-tyrosine, N-alpha-Fmoc-O-benzyl-tyrosine, N-alpha-Fmoc-O-2,6-dichlorobenzyl-tyrosine, N-alpha-Fmoc-O-ethyl-tyrosine, N-alpha-Fmoc-O-methyl-tyrosine, N-alpha-Fmoc-O-tert-butyl-tyrosine, N-alpha-Fmoc-O-benzyl-threonine, and N-alpha-Fmoc-threonine or derivatives thereof.

In certain embodiments, the disclosure relates to any of the above carboxylic acids that are a S-(2-(isopropylcarbamoyl)-4-nitrophenyl)thioate, S-(2-(isopropylcarbamoyl)-4-sulfonic acid)thioate, S-(2-(alkylcarbamoyl)phenyl)thioate, S-(2-(phenylcarbamoyl)phenyl)thioate, S-(2-((2,6-dimethylphenyl)carbamoyl)phenyl)thioate, S-(2-((2,6-dimethylphenyl)carbamoyl)-4-nitrophenyl)thioate or derivative thereof.

In some embodiments, the disclosure relates to a compound comprising the following formula:

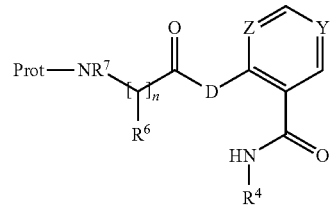

or salts thereof wherein,

Prot is a protecting group, peptide, or linker to a substrate or biological material, or $R^8$;

n is 1, 2, 3, 4, 5, or 6;

D is sulfur, selenium, or tellurium;

Y is N, CH, or C—$R^5$;

Z is N or CH $R^4$ is selected from alkyl, alkenyl, alkanoyl, cyano, dialkylamino, carbocyclyl, aryl, and heterocyclyl wherein $R^4$ is optionally substituted with one or more, the same or different, $R^{40}$ or $R^{41}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, sulfonate, cyano, hydroxy, amino, mercapto, formyl, carboxy, sulfoxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

each $R^6$ is independently selected from hydrogen, alkyl, hydroxyalkyl, thiolalkyl, aminoalkyl, selenoalkyl, carboxylalkyl, aryl, or heterocyclyl, and wherein $R^6$ is optionally substituted by one or more, the same or different, $R^{60}$;

$R^7$ is selected from hydrogen, alkyl, acyl, or $R^7$ and Prot and the attached atoms form a protecting group comprising a 4 to 7 member heterocyclic ring such as a succinimide, maleimide, or phthalimide which may be substituted with one or more, the same or different, substituents, such as one or more, the same or different, $R^{60}$ or or $R^6$ and $R^7$ and the atoms to which they are attached to form a 4-7 membered heterocyclic ring optionally substituted with one or more, the same or different, $R^{60}$;

$R^{60}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{60}$ is optionally substituted with $R^{61}$;

$R^{61}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl; and $R^8$ is alkyl, alkanoyl, formyl, alkylcarboxy, alkylcarbamoyl wherein $R^8$ is optionally substituted with one or more, the same or different, $R^{80}$;

$R^{80}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{80}$ is optionally substituted with one or more, the same or different, $R^{81}$; and $R^{81}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^5$ is an electron with drawing group selected from nitro, quaternary amine, trihalo alkyl, trifluoromethyl, cyano, alkanoyl, formyl, carboxy, carbamoyl, alkylsulfinyl, alkylsulfonyl, and arylsulfonyl wherein $R^5$ is optionally substituted with one or more, the same or different, $R^{50}$.

In some embodiments, $R^4$ is aryl or heteroaryl wherein $R^4$ is optionally substituted with one or more, the same or different, $R^{40}$ or $R^{41}$.

In some embodiments, the disclosure relates to a compound comprising the following formula:

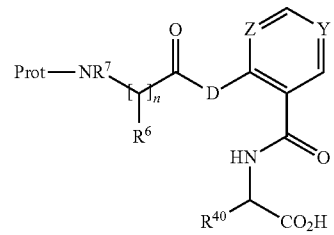

or salts thereof wherein,

Prot is a protecting group, peptide, or linker to a substrate or biological material, or $R^8$;

n is 1, 2, 3, 4, 5, or 6;

D is sulfur, selenium, or tellurium;

Y is N, CH, or C—$R^5$;

Z is N or CH $R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, cyano, hydroxy, amino, mercapto, sulfonate, formyl, carboxy, carbamoyl, alkoxy, alkylthio, alkylamino, dialkylamino, sulfoxy, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

each $R^6$ is independently selected from hydrogen, alkyl, hydroxyalkyl, thiolalkyl, aminoalkyl, selenoalkyl, carboxylalkyl, aryl, or heterocyclyl, and wherein $R^6$ is optionally substituted by one or more, the same or different, $R^{60}$;

$R^7$ is selected from hydrogen, alkyl, acyl, or $R^7$ and Prot and the attached atoms form a protecting group comprising a 4 to 7 member heterocyclic ring such as a succinimide, maleimide, or phthalimide which may be substituted with one or more, the same or different, substituents, such as one or more, the same or different, $R^{60}$ or or $R^6$ and $R^7$ and the atoms to which they are attached to form a 4-7 membered heterocyclic ring optionally substituted with one or more, the same or different, $R^{60}$;

$R^{60}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{60}$ is optionally substituted with $R^{61}$;

$R^{61}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl; and $R^8$ is alkyl, alkanoyl, formyl, alkylcarboxy, alkylcarbamoyl wherein $R^8$ is optionally substituted with one or more, the same or different, $R^{80}$;

$R^{80}$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{80}$ is optionally substituted with one or more, the same or different, $R^{81}$; and $R^{81}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, $R^5$ is an electron with drawing group selected from nitro, sulfonate, quaternary amine, trihalo alkyl, trifluoromethyl, cyano, alkanoyl, formyl, carboxy, carbamoyl, alkylsulfinyl, alkylsulfonyl, and arylsulfonyl wherein $R^5$ is optionally substituted with one or more, the same or different, $R^{50}$.

In certain embodiment, the amine or the alcohol has the following formula:

wherein,
X is O, NH, or $NR^3$;
$R^2$ is selected from alkyl, alkenyl, alkanoyl, cyano, carboxy, alkylamino, dialkylamino, carbocyclyl, aryl, and heterocyclyl wherein $R^2$ is optionally substituted with one or more, the same or different, $R^{20}$ or $R^{25}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$ or $R^{25}$;

$R^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{21}$ is optionally substituted with one or more, the same or different, $R^{22}$ or $R^{25}$;

$R^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{22}$ is optionally substituted with one or more, the same or different, $R^{23}$ or $R^{25}$;

$R^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{23}$ is optionally substituted with one or more, the same or different, $R^{24}$ or $R^{25}$;

$R^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{24}$ is optionally substituted with one or more, the same or different, $R^{25}$;

$R^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^3$ is selected from alkyl, alkenyl, alkanoyl, cyano, carbocyclyl, aryl, and heterocyclyl wherein $R^3$ is optionally substituted with one or more, the same or different, $R^{30}$ or $R^{31}$;

$R^{30}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{30}$ is optionally substituted with one or more, the same or different, $R^{31}$; and $R^{31}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the amide or ester has the formula

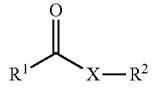

wherein,

X is O, NH, or NR$^3$;

R$^1$ is selected from alkyl, alkenyl, alkanoyl, cyano, carboxy, alkylamino, dialkylamino, carbocyclyl, aryl, and heterocyclyl wherein R$^1$ is optionally substituted with one or more, the same or different, R$^{10}$ or R$^{15}$;

R$^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{10}$ is optionally substituted with one or more, the same or different, R$^{11}$ or R$^{15}$;

R$^{11}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{11}$ is optionally substituted with one or more, the same or different, R$^{12}$ or R$^{15}$;

R$^{12}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{12}$ is optionally substituted with one or more, the same or different, R$^{13}$ or R$^{15}$;

R$^{13}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{13}$ is optionally substituted with one or more, the same or different, R$^{14}$ or R$^{15}$;

R$^{14}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{14}$ is optionally substituted with one or more, the same or different, R$^{15}$;

R$^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

R$^2$ is selected from alkyl, alkenyl, alkanoyl, cyano, carboxy, alkylamino, dialkylamino, carbocyclyl, aryl, and heterocyclyl wherein R$^2$ is optionally substituted with one or more, the same or different, R$^{20}$ or R$^{25}$;

R$^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{20}$ is optionally substituted with one or more, the same or different, R$^{21}$ or R$^{25}$;

R$^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{21}$ is optionally substituted with one or more, the same or different, R$^{22}$ or R$^{25}$;

R$^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{22}$ is optionally substituted with one or more, the same or different, R$^{23}$ or R$^{25}$;

R$^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{23}$ is optionally substituted with one or more, the same or different, R$^{24}$ or R$^{25}$;

R$^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{24}$ is optionally substituted with one or more, the same or different, R$^{25}$;

R$^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

R$^3$ is selected from alkyl, alkenyl, alkanoyl, cyano, carbocyclyl, aryl, and heterocyclyl wherein R$^3$ is optionally substituted with one or more, the same or different, R$^{30}$ or R$^{31}$;

R$^{30}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{30}$ is optionally substituted with one or more, the same or different, R$^{31}$; and R$^{31}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the disclosure relates to methods of forming a ketone comprising mixing a) a compound comprising a carboxylic acid, b) a trialkylphosphite, c) an carbon nucleophile or boronic acid, d) a sulfur, amide heterocycle, and e) copper under conditions such that a ketone is formed.

In certain embodiments, the disclosure relates to mixing a carbon nucleophile under conditions such that a ketone is formed. In further embodiments, the nucleophile is an alkyl, aryl, or heteroaryl optionally substituted from an alkyl boronic acid ester or an alkyl, aryl, or heteroaryl optionally substituted stannane which react via a copper catalyzed reaction with boronic acids (esters) or stannanes.

In certain embodiments, the boronic acid has the following formula:

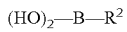

(HO)$_2$—B—R$^2$ wherein,

R$^2$ is selected from alkyl, alkenyl, alkanoyl, carboxy, carbocyclyl, aryl, and heterocyclyl wherein R$^2$ is optionally substituted with one or more, the same or different, R$^{20}$ or R$^{25}$;

R$^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{20}$ is optionally substituted with one or more, the same or different, R$^{21}$ or R$^{25}$;

R$^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{21}$ is optionally substituted with one or more, the same or different, R$^{22}$ or R$^{25}$;

R$^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{22}$ is optionally substituted with one or more, the same or different, R$^{23}$ or R$^{25}$;

R$^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{23}$ is optionally substituted with one or more, the same or different, R$^{24}$ or R$^{25}$;

R$^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{24}$ is optionally substituted with one or more, the same or different, R$^{25}$;

R$^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the ketone has the formula

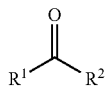

wherein,

R$^1$ is selected from alkyl, alkenyl, alkanoyl, carboxy, carbocyclyl, aryl, and heterocyclyl wherein R$^1$ is optionally substituted with one or more, the same or different, R$^{10}$ or R$^{15}$;

R$^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{10}$ is optionally substituted with one or more, the same or different, R$^{11}$ or R$^{15}$;

R$^{11}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{11}$ is optionally substituted with one or more, the same or different, R$^{12}$ or R$^{15}$;

R$^{12}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{12}$ is optionally substituted with one or more, the same or different, R$^{13}$ or R$^{15}$;

R$^{13}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{13}$ is optionally substituted with one or more, the same or different, R$^{14}$ or R$^{15}$;

R$^{14}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{14}$ is optionally substituted with one or more, the same or different, R$^{15}$;

R$^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

R$^2$ is selected from alkyl, alkenyl, alkanoyl, cyano, carboxy, alkylamino, dialkylamino, carbocyclyl, aryl, and heterocyclyl wherein R$^2$ is optionally substituted with one or more, the same or different, R$^{20}$ or R$^{25}$;

R$^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{20}$ is optionally substituted with one or more, the same or different, R$^{21}$ or R$^{25}$;

R$^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{21}$ is optionally substituted with one or more, the same or different, R$^{22}$ or R$^{25}$;

R$^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein R$^{22}$ is optionally substituted with one or more, the same or different, R$^{23}$ or R$^{25}$;

R$^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{23}$ is optionally substituted with one or more, the same or different, $R^{24}$ or $R^{25}$;

$R^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{24}$ is optionally substituted with one or more, the same or different, $R^{25}$; and $R^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl. methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, the disclosure relates to method of forming a carbon-carbon bond comprising mixing a trisubstituted phosphite; a sulfur, amide heterocycle; and silylating agent in a solvent followed by adding a compound comprising an hydroxyalkyl optionally substituted with one or more, the same or different, substituent under conditions such that a thiol intermediate is formed and mixing the thiol intermediate with copper, a carbon nucleophile and optionally another metal under conditions such athat a carbon-carbon bond is formed between the carbon of the hydroxyl alkyl and the carbond nucleophile.

In certain embodiments the disclosure relates to method of forming a carbon-carbon bond comprising mixing a) an hydroxyalkyl, b) a trisubstituted phosphite; c) a catalytic heterocycle; d) a carbon nucleophile and e) $Z(R^9)_3$ wherein Z is selected from P, As, Sb, Bi and $R^9$ is individually at each occurrence alkyl, aryl, or heteroaryl optionally substituted with one or more, the same or different, substitutents under conditions such that carbon to carbon bond is formed between the nucleophile and the alkyl. In certain embodiments, the carbon nucleophile is cardioxide or carbon monoxide.

EXAMPLES

The Desulfitative Redox Catalysts

Figure 10:
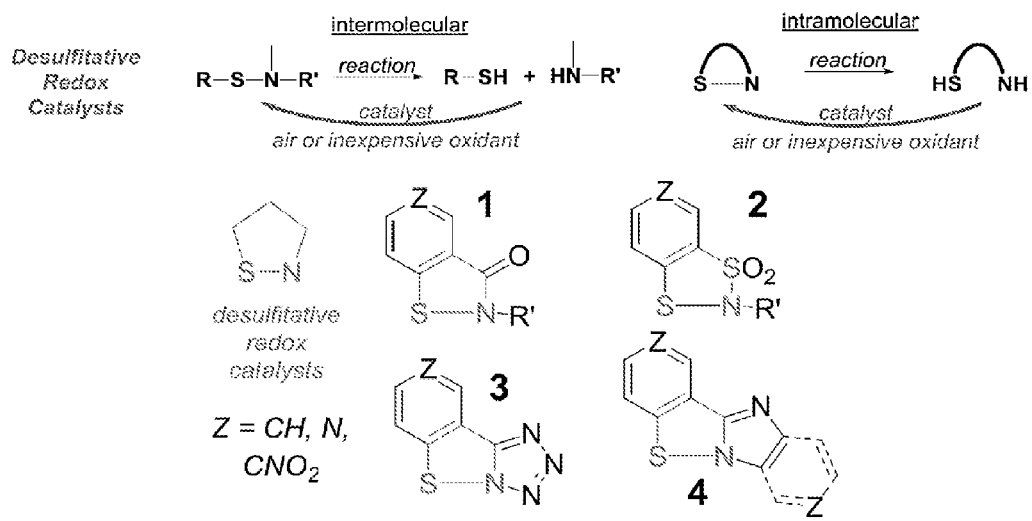
FIG. 10 illustrates additional embodiments of contemplated catalysts.
Figure 11:
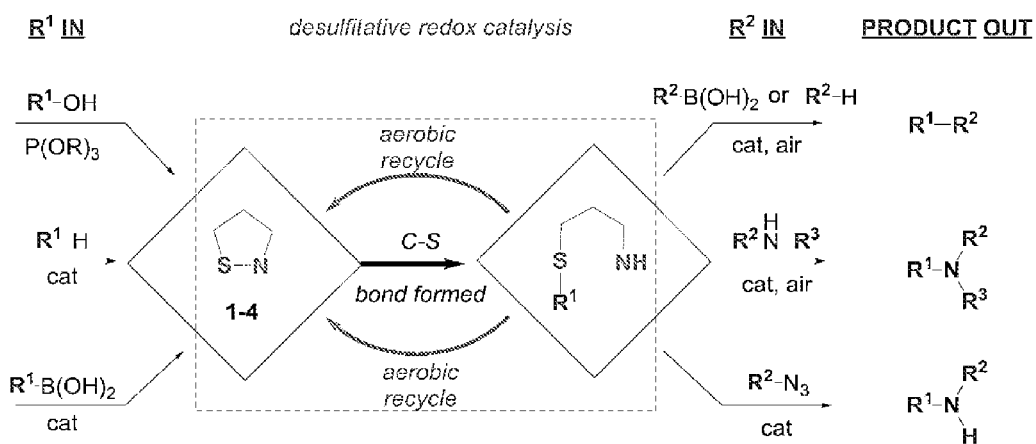
FIG. 11 illustrates desulfitative redox catalysis and use in C—C and C—N bond formation. Desulfitative redox catalysis is contemplated to be more general than useful for amide and peptide bond construction. It has been used to construct carbon-carbon as well as carbon-nitrogen bonds and may be extended to the construction of carbon-oxygen bonds as well.

The desulfitative redox catalysts of this disclosure cover any molecular system bearing a sulfur to nitrogen bond (a sulfenamide) that is generated either in an intramolecular or an intramolecular fashion in the presence of a catalyst and either air (O2) or an oxidant (FIG. 10). Four representative series of "intramolecular" desulfitative redox catalysts are shown in FIG. 10 (1-4). Each of the desulfitative redox catalysts (1, 2, 3, and 4) possesses heteroatom O- and N-control points at which either protic or Lewis acids can potentially influence the reactivity of the individual steps of the desulfitative redox cycle: (1) thioester C—S bond formation, and (2) subsequent desulfitative C—N bond formation with simultaneous oxidative regeneration of the desulfitative redox catalysts. Electronic tuning of reactivity is also feasible by variation of substituents Z=CH, CNO2, and N at the positions of substitution indicated in FIG. 10.

The direct conversion of carboxylic acids and benzoisothiazolones (1, FIG. 10) into the corresponding thioesters can be done by a Mukaiyama-like redox dehydration using benzoisothiazolones, 1, and a reactive triorganophosphine (PPh3, PBu3). This protocol was improved by replacing the triorganophosphine with the phosphite, P(OMe)3. Using this phosphite avoids the use of the more reactive phosphines for the redox dehydration, and simplifies workup and purification because the P(OMe)3 is transformed into easily removed, watersoluble trimethylphosphate. Surprisingly, the use of a phosphite, e.g., P(OMe)3, in generating the thioester is not compromised by Arbuzov-like demethylation side reactions, a known problem in azodicarboxylate-based Mitsunobu reactions. See Véliz et al. Mitsunobu reactions of nucleoside analogs using triisopropyl phosphite—DIAD. Tetrahedron Lett. 2006, 47, 3153-3156. Interference from Arubzov like side-reactions with phosphite reagents may be the reason that phosphites have not yet been explored in generating thioesters.

One can use open-to-air reaction of amines with thioesters, generated from a carboxylic acid, P(OMe)3, and a desulfitative redox catalyst 1-4, to give amides that takes place coincident with aerobic regeneration. This represents an economical and practical "desulfitative redox catalytic route to amides directly from carboxylic acids, amines, air, and P(OMe)3 under mild conditions.

Thioester generation and desulfitative amide/peptide bond formation, can be linked in one pot without isolation of intermediates (batch-mode recycle). It is desireable if both reaction steps can take place open to air under the same or similar conditions, thus allowing the desulfitative redox catalyst to be used catalytically rather than in a batch recycle mode. Solid-phase supported catayulic systems are useful in fully catalytic mode applications of the desulfitative redox catalysts. Attachment procedures can be pursued through the amide/sulfonamide R' group of 1 and 2, and through R" of 1-4 where Z=CSO2NHR" (Z in FIG. 10). See Testero & Mata, Prospect of Metal-Catalyzed C—C Forming Cross-Coupling Reactions in Modern Solid-Phase Organic Synthesis. J. Comb. Chem., 2008, 10, (4), 487-497.

The reaction system described in this disclosure may proceed in a mode that uses only catalytic quantities of 1-4. It is desireable for the the phosphite to react faster with the desulfitative redox catalyst/$R^1CO_2H$ than in its direct, aerobic oxidation to trimethylphosphate, and the Cu catalyst turn over rapidly in the presence of trimethylphosphite (and trimethylphosphate as it builds up). In certain embodiments, the disclosure contemplates the four redox catalysts, 1-4, and their resulting thioesters. Redox active metal catalysts other than Cu may be used (e.g., Fe, Co, Mo) to drive the aerobic cross-coupling reaction.

The use of desulfitative redox catalysis for amide bond formation using desulfitative redox catalyst 1 is provided below.

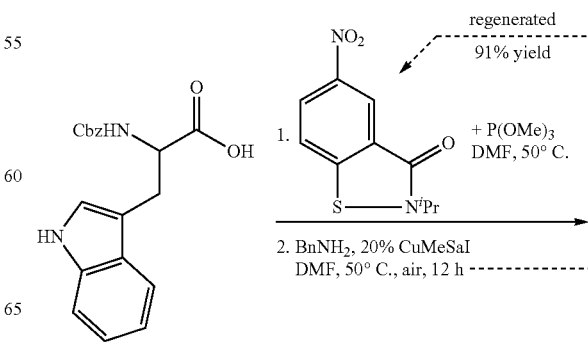

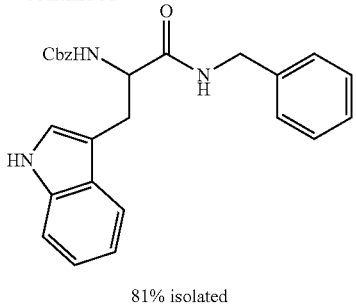

81% isolated

What we claim:

1. A method of catalyzing a coupling reaction comprising mixing
   a) a compound comprising a hydroxy group,
   b) a trisubstituted phosphite,
   c) a nucleophile, and
   d) a catalytic heterocycle comprising two bonded heteroatoms wherein one heteroatom is a nitrogen and the second heteroatom is not nitrogen,
   under conditions such that a compound is formed comprising the nucleophile in place of the hydroxy group.

2. The method of claim 1, wherein mixing includes a copper.

3. The method of claim 1, wherein the trisubstituted phosphite is trialkylphosphite selected from trimethylphosphite, triethylphosphite, tripropylphosphite, triisopropylphosphite, tributyl phosphite, and tert-butylphoshpite.

4. The method of claim 1, wherein mixing is done under conditions such that an amide, an amine, an ester, an ether, a ketone, or other carbon to carbon bond is formed.

5. The method of claim 1, wherein the compound comprising a hydroxy group is primary or secondary alcohol or a carboxylic acid.

6. The method of claim 1, wherein the nucleophile comprising a hydrogen group is a primary or secondary amine, or primary or secondary alcohol, or boronic acid.

7. The method of claim 1, wherein the catalytic heterocycle is benzoisothiazolone.

8. The method of claim 1, wherein the catalystic heterocycle linked through a linking group to a silicate, glass, polymer, metal, particle, nanoparticle, magnetic bead, nanostructure, or other solid support.

9. A method of forming an amide or ester comprising mixing
   a) a compound comprising a carboxylic acid,
   b) a trialkylphosphite,
   c) an amine or an alcohol,
   d) a catalytic sulfur, amide heterocycle, and
   e) copper under conditions such that an amide or an ester is formed.

10. The method of claim 9, wherein the compound has the following formula:

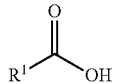

wherein,
R¹ is selected from alkyl, alkenyl, alkanoyl, cyano, carboxy, alkylamino, dialkylamino, carbocyclyl, aryl, heterocyclyl, amino acid, polypeptide and wherein $R^1$ is optionally substituted with one or more, the same or different, $R^{10}$ or $R^{15}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$ or $R^{15}$;

$R^{11}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with one or more, the same or different, $R^{12}$ or $R^{15}$;

$R^{12}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{12}$ is optionally substituted with one or more, the same or different, $R^{13}$ or $R^{15}$;

$R^{13}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{13}$ is optionally substituted with one or more, the same or different, $R^{14}$ or $R^{15}$;

$R^{14}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with one or more, the same or different, $R^{15}$; and $R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

11. The method of claim 9, wherein the amine or the alcohol has the following formula:

wherein,
X is O, NH, or $NR^3$;
$R^2$ is selected from alkyl, alkenyl, alkanoyl, cyano, carboxy, alkylamino, dialkylamino, carbocyclyl, aryl, and heterocyclyl wherein $R^2$ is optionally substituted with one or more, the same or different, $R^{20}$ or $R^{25}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$ or $R^{25}$;

$R^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{21}$ is optionally substituted with one or more, the same or different, $R^{22}$ or $R^{25}$;

$R^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{22}$ is optionally substituted with one or more, the same or different, $R^{23}$ or $R^{25}$;

$R^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{23}$ is optionally substituted with one or more, the same or different, $R^{24}$ or $R^{25}$;

$R^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{24}$ is optionally substituted with one or more, the same or different, $R^{25}$;

$R^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^3$ is selected from alkyl, alkenyl, alkanoyl, cyano, carbocyclyl, aryl, and heterocyclyl wherein $R^3$ is optionally substituted with one or more, the same or different, $R^{30}$ or $R^{31}$;

$R^{30}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{30}$ is optionally substituted with one or more, the same or different, $R^{31}$; and $R^{31}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

12. The method of claim 9, wherein the sulfur, amide heterocycle has the following formula:

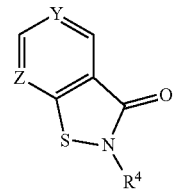

wherein,

Y is N, CH, or C—$R^5$;

Z is N or CH $R^4$ is selected from alkyl, alkenyl, alkanoyl, cyano, dialkylamino, carbocyclyl, aryl, and heterocyclyl wherein $R^4$ is optionally substituted with one or more, the same or different, $R^{40}$ or $R^{41}$;

$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;

$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;

$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

13. The method of claim 10, wherein the amide or ester has the formula

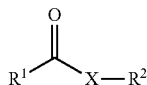

wherein,

X is O, NH, or $NR^3$;

$R^1$ is selected from alkyl, alkenyl, alkanoyl, cyano, carboxy, alkylamino, dialkylamino, carbocyclyl, aryl, and heterocyclyl wherein $R^1$ is optionally substituted with one or more, the same or different, $R^{10}$ or $R^{15}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$ or $R^{15}$;

$R^{11}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with one or more, the same or different, $R^{12}$ or $R^{15}$;

$R^{12}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{12}$ is optionally substituted with one or more, the same or different, $R^{13}$ or $R^{15}$;

$R^{13}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{13}$ is optionally substituted with one or more, the same or different, $R^{14}$ or $R^{15}$;

$R^{14}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with one or more, the same or different, $R^{15}$;

$R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from alkyl, alkenyl, alkanoyl, cyano, carboxy, alkylamino, dialkylamino, carbocyclyl, aryl, and heterocyclyl wherein $R^2$ is optionally substituted with one or more, the same or different, $R^{20}$ or $R^{25}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$ or $R^{25}$;

$R^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{21}$ is optionally substituted with one or more, the same or different, $R^{22}$ or $R^{25}$;

$R^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{22}$ is optionally substituted with one or more, the same or different, $R^{23}$ or $R^{25}$;

$R^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{23}$ is optionally substituted with one or more, the same or different, $R^{24}$ or $R^{25}$;

$R^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{24}$ is optionally substituted with one or more, the same or different, $R^{25}$;

$R^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^3$ is selected from alkyl, alkenyl, alkanoyl, cyano, carbocyclyl, aryl, and heterocyclyl wherein $R^3$ is optionally substituted with one or more, the same or different, $R^{30}$ or $R^{31}$;

$R^{30}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{30}$ is optionally substituted with one or more, the same or different, $R^{31}$; and $R^{31}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

14. A method of forming a ketone comprising mixing
a) a compound comprising a carboxylic acid,
b) a trialkylphosphite,
c) an boronic acid,
d) a sulfur, amide heterocycle, and
e) copper under conditions such that a ketone is formed.

15. The method of claim 14, wherein the sulfur, amide heterocycle has the following formula:

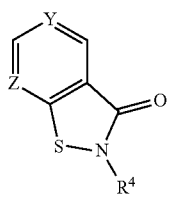

wherein,
Y is N, CH, or C—$R^5$;
Z is N or CH
$R^4$ is selected from alkyl, alkenyl, alkanoyl, cyano, dialkylamino, carbocyclyl, aryl, and heterocyclyl wherein $R^4$ is optionally substituted with one or more, the same or different, $R^{40}$ or $R^{41}$;
$R^{40}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{40}$ is optionally substituted with one or more, the same or different, $R^{41}$;
$R^{41}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;
$R^5$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^5$ is optionally substituted with one or more, the same or different, $R^{50}$;
$R^{50}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

16. The method of claim 15, wherein $R^5$ is an electron with drawing group selected from nitro, quaternary amine, trihalo alkyl, trifluoromethyl, cyano, alkanoyl, formyl, carboxy, carbamoyl, alkylsulfinyl, alkylsulfonyl, and arylsulfonyl wherein $R^5$ is optionally substituted with one or more, the same or different, $R^{50}$.

17. The method of claim 14, wherein the compound comprising a carboxylic acid is an amino acid, polypeptide, or a compound having the following formula:

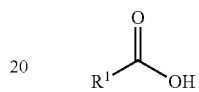

wherein,
$R^1$ is selected from alkyl, alkenyl, alkanoyl, carboxy, carbocyclyl, aryl, and heterocyclyl wherein $R^1$ is optionally substituted with one or more, the same or different, $R^{10}$ or $R^{15}$;
$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$ or $R^{15}$;
$R^{11}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with one or more, the same or different, $R^{12}$ or $R^{15}$;
$R^{12}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{12}$ is optionally substituted with one or more, the same or different, $R^{13}$ or $R^{15}$;
$R^{13}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{13}$ is optionally substituted with one or more, the same or different, $R^{14}$ or $R^{15}$;
$R^{14}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with one or more, the same or different, $R^{15}$; and
$R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

18. The method of claim 15, wherein boronic acid has the following formula:

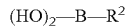

wherein, $R^2$ is selected from alkyl, alkenyl, alkanoyl, carboxy, carbocyclyl, aryl, and heterocyclyl wherein $R^2$ is optionally substituted with one or more, the same or different, $R^{20}$ or $R^{25}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$ or $R^{25}$;

$R^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{21}$ is optionally substituted with one or more, the same or different, $R^{22}$ or $R^{25}$;

$R^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{22}$ is optionally substituted with one or more, the same or different, $R^{23}$ or $R^{25}$;

$R^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{23}$ is optionally substituted with one or more, the same or different, $R^{24}$ or $R^{25}$;

$R^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{24}$ is optionally substituted with one or more, the same or different, $R^{25}$;

$R^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

19. The method of claim 15, wherein the ketone has the formula

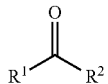

wherein, $R^1$ is selected from alkyl, alkenyl, alkanoyl, carboxy, carbocyclyl, aryl, and heterocyclyl wherein $R^1$ is optionally substituted with one or more, the same or different, $R^{10}$ or $R^{15}$;

$R^{10}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{10}$ is optionally substituted with one or more, the same or different, $R^{11}$ or $R^{15}$;

$R^{11}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{11}$ is optionally substituted with one or more, the same or different, $R^{12}$ or $R^{15}$;

$R^{12}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{12}$ is optionally substituted with one or more, the same or different, $R^{13}$ or $R^{15}$;

$R^{13}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{13}$ is optionally substituted with one or more, the same or different, $R^{14}$ or $R^{15}$;

$R^{14}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{14}$ is optionally substituted with one or more, the same or different, $R^{15}$;

$R^{15}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl;

$R^2$ is selected from alkyl, alkenyl, alkanoyl, cyano, carboxy, alkylamino, dialkylamino, carbocyclyl, aryl, and heterocyclyl wherein $R^2$ is optionally substituted with one or more, the same or different, $R^{20}$ or $R^{25}$;

$R^{20}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{20}$ is optionally substituted with one or more, the same or different, $R^{21}$ or $R^{25}$;

$R^{21}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{21}$ is optionally substituted with one or more, the same or different, $R^{22}$ or $R^{25}$;

$R^{22}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{22}$ is optionally substituted with one or more, the same or different, $R^{23}$ or $R^{25}$;

$R^{23}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{23}$ is optionally substituted with one or more, the same or different, $R^{24}$ or $R^{25}$;

$R^{24}$ is selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^{24}$ is optionally substituted with one or more, the same or different, $R^{25}$; and $R^{25}$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl.methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

\* \* \* \* \*